United States Patent [19]
Minnich

[11] Patent Number: 6,075,060
[45] Date of Patent: Jun. 13, 2000

[54] TRANS OLEFINIC DIOLS WITH SURFACTANT PROPERTIES

[75] Inventor: Kristen Elaine Minnich, Allentown, Pa.

[73] Assignee: Air Products and Chemicals, Inc., Allentown, Pa.

[21] Appl. No.: 09/034,032

[22] Filed: Mar. 3, 1998

[51] Int. Cl.[7] .............................. B01F 17/38; C07G 31/20
[52] U.S. Cl. .............................. 516/28; 516/72; 516/204; 516/917; 568/857; 106/311; 106/31.86; 106/31.89; 510/524; 510/535
[58] Field of Search ................................ 516/72, 204, 28, 516/917; 568/857; 106/311, 326, 31.25, 31.26, 31.85, 31.86, 31.89; 510/524, 535

[56] References Cited

U.S. PATENT DOCUMENTS

| | | | |
|---|---|---|---|
| 2,893,913 | 7/1959 | Wiedow | 516/72 |
| 2,997,447 | 8/1961 | Russell et al. | 516/72 |
| 3,268,593 | 8/1966 | Carpenter et al. | 510/535 |
| 3,819,522 | 6/1974 | Zmoda et al. | 510/524 |
| 4,929,683 | 5/1990 | Kennedy et al. | 525/268 |
| 5,053,561 | 10/1991 | Bender et al. | 568/857 |
| 5,747,443 | 5/1998 | Wahl et al. | 510/515 |

OTHER PUBLICATIONS

*Kirk–Othmer Encyclopedia of Chemical Technology*, 4th ed., Wiley, 1991, (Month Unknown) vol. 1, pp. 206–209
John R. Johnson and O. H. Johnson, in *Journal of the American Chemical Society*, vol. 62 (Oct. 1940), pp. 2615–2620.

*Primary Examiner*—Richard D. Lovering
*Assistant Examiner*—Daniel S. Metzmaier
*Attorney, Agent, or Firm*—Mary E. Bongiorno

[57] ABSTRACT

An aqueous composition and a method of applying an aqueous composition to a surface in which the surface active properties of the composition are improved through addition of a new class of surfactants based on the trans isomers of olefinic diols having the formula:

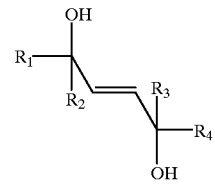

wherein each of $R_1$, $R_2$, $R_3$, and $R_4$ is the same or a different C1 to C9 linear or branched alkyl group and the total number of carbons atoms in the olefinic diol is between 12 and 17. The compounds are useful in lowering the equilibrium surface tension of aqueous organic compositions; for example, those used in coatings, inks and adhesives.

16 Claims, No Drawings

TRANS OLEFINIC DIOLS WITH SURFACTANT PROPERTIES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

Several olefinic diols of the general formula:

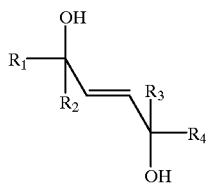

in which $R_1$, $R_2$, $R_3$, and $R_4$ are the same or different alkyl groups, are known. Pure trans diols of the above formula, in which the R groups are the same or different $C_1$ to $C_5$ alkyl groups, have been reported to be useful as starting compounds for the synthesis of initiator-transfer agents for cationic polymerization processes.

Of known olefinic diols, butenediol has been described as the only commercially available olefinic diol with primary hydroxyl groups (*Kirk-Othmer Encyclopedia of Chemical Technology*, 4$^{th}$ ed., Wiley, 1991, Vol. 1, pages 206–209.) Commercially, the cis isomer of butenediol is almost exclusively formed, although suitable conditions are known to lead to the cis or trans isomers of olefinic-1,4-diols. For example, John R. Johnson and O. H. Johnson, in *Journal of the American Chemical Society*, Vol. 62 (October 1940), pages 2615–2620, describe the preparation of cis and trans forms of 2,5, dimethyl-3-hexene-2,5-diol. U.S. Pat. No. 5,053,561 (Bender et al, 1991) describes a method for separating the cis and trans isomers of olefinic diols, such as 1,1,4,4-tetraalkyl-2-butene-1,4-diols, by liquid-liquid extraction.

BRIEF SUMMARY OF THE INVENTION

This invention is directed to water based compositions containing an organic material and having reduced equilibrium surface tension by incorporation of trans olefinic diols; specifically, trans isomers of olefinic diols having the formula:

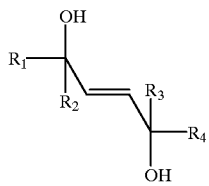

wherein each of $R_1$, $R_2$, $R_3$, and $R_4$ is the same or a different $C_1$ to $C_9$ linear or branched alkyl group and the total number of carbons atoms in the compound is between 12 and 17.

Also provided is a method of applying a water-based organic compound-containing composition to a surface, the composition containing an effective amount of an above described trans olefinic diol for reducing the equilibrium surface tension of the composition.

These trans-olefinic diols display superior equilibrium surface tension properties compared to their cis isomers. In addition, the trans-olefinic-1,4-diols show good solubility and low foam properties.

Because of their excellent surfactant properties, low foam characteristics, and good solubility in water, the trans diols of this invention will be useful in many areas in which reduction in equilibrium surface tension and low foam in aqueous organic systems are important. For example, these materials would be particularly useful as surfactants in water-based compositions containing an organic compound; for example, coatings, inks, and adhesives. They may also have applicability in soaps, water-based perfumes, shampoos, and various detergents.

BRIEF DESCRIPTION OF SEVERAL VIEWS OF THE DRAWINGS

Not applicable.

DETAILED DESCRIPTION OF THE INVENTION

This invention is directed to use of the trans isomers of olefinic diols having the formula:

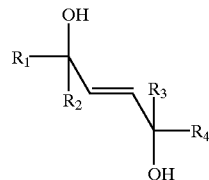

wherein each of $R_1$, $R_2$, $R_3$, and $R_4$ is the same or different C1 to C9 linear or branched alkyl group and the total number of carbons atoms in the molecule is between 12 and 17, as surfactants in water-based organic systems. An effective amount of the trans-olefinic diols of this invention will reduce the equilibrium surface tension of water-based compositions containing an organic compound; for example, coatings, inks, and adhesives.

Cis and trans isomers of olefinic diols have been reported to have very similar physical properties due to their structural similarity; however, a significant difference was found between cis and trans isomers with regard to solubility in water and surface active properties in aqueous systems.

For use as a surfactant, it is desirable that a 0.1 wt % aqueous solution of the trans olefinic diols of this invention demonstrate an equilibrium surface tension (EST) of 50 dynes/cm or less; preferably 35 dynes/cm or less. The equilibrium surface tension is measured using the maximum-bubble-pressure method at 23° C. and 1 bubble/second. This method is described in *Langmuir*, Vol. 2 (1986), pp. 428–432. When measured at the solubility limit of the surfactant, an equilibrium surface tension of 40 dynes/cm or less is desired; preferably 35 dynes/cm or less.

Effective surfactants need to have a good balance of water solubility and surface tension properties. Generally, in the practice of this invention it is desirable to use trans olefinic-1,4-diols having a solubility of 0.005 to 2.0 wt %; preferably 0.01 to 1.0 wt %.

The trans olefinic diols of this invention can be prepared by any of several known methods. For example, reduction of acetylenic diols using a heterogeneous catalyst; reaction of trans-3-hexene-2,5-dione with alkyl lithium reagents; reaction of diethyl fumarate with an alkyl lithium; free radical addition of a secondary alcohol to an acetylene compound, such as a 2-alkyl-3-bytyne-2-ol; or by photochemical or catalytic isomerization of the cis isomers.

It was found in this invention that the most suitable $R_1$, $R_2$, $R_3$, and $R_4$ alkyl groups in the trans olefinic diol are those that result in an olefinic product with a total of 12 to 17 total carbon atoms; preferably 14 to 16 carbon atoms. Outside this range of carbon atoms, either above 17 carbons or below 12 carbons, the product showed an equilibrium surface tension above 50 dynes/cm for an 0.1 wt % solution. Examples of suitable olefinic diol products include those in which the R groups are a combination of methyl, ethyl, n-propyl, isopropyl, n-butyl, isobutyl, tert-butyl, n-pentyl and isopentyl.

Representative compounds of this new class of nonionic surfactants are trans isomers of:

3,6-diethyl-4-octene-3,6-diol;
2,4,7,9-tetramethyl-5-decene-4,7-diol;
2,5,8,11-tetramethyl-6-dodecene-5,8-diol; and
5,8-dimethyl-6-dodecene-5,8-diol.

The cis and trans isomers can be separated using liquid—liquid extraction processes, such as those described in U.S. Pat. No. 5,053,561 which is hereby incorporated by reference. Extraction is effected using a polar and a non-polar phase, in which case the cis and the trans isomers accumulate to varying extents in the two phases such that the selective separation of the trans isomer is possible.

The trans-olefinic diols of this invention may be employed in any process, or incorporated in any composition, where it is desired to take advantage of their superior surface active properties. They are especially useful in organic-containing aqueous compositions.

The amount of the trans-olefinic diol that is effective in reducing the equilibrium surface tension of a water-based, organic-containing composition will vary depending on the diol used and the use to which the aqueous composition will be put. In general, the diol may be employed in proportions from about 0.01 to 1 wt % of the aqueous composition to which it is added.

The invention will be further clarified by a consideration of the following examples, which are intended to be purely exemplary of the use of the invention.

EXAMPLES 1 AND 2

Olefinic Diols with 10 or less Carbons

An acetylenic-1,4-diol (10 g), 5% Pd/C (0.025 g) and hexane (40 ml) were charged to a stainless steel Parr reactor. In Example 1, the acetylenic diol is 2,5-dimethyl-3-hexyne-2,5-diol, and, in Example 2, it is 3,6-dimethyl-4-octyne-3,6-diol. The reactor was pressurized to 50 psi hydrogen at room temperature and stirred. The reductions which were exothermic stopped preferentially at olefin. The reaction mixtures contained approximately a 90:8:2 ratio of cis:trans:alkane. The GC area percents for the isomers obtained are listed in Table 1. The cis and trans isomers were isolated by column chromatography, eluting with 1:1 hexane:ethyl acetate or 2% methanol/methylene chloride solvent.

TABLE 1

GC Area Percent of Products from Reduction of Acetylenic Diols

| Example | Structure | Cis | Trans | Alkane |
|---|---|---|---|---|
| 1 | (structure) | 88 | 8 | 3 |
| 2 | (structure) | 83 | 9 | 7 |

The equilibrium surface tension was measured using the maximum-bubble-pressure method at 23° C. and 1 bubble/second at 0.1 wt %. The results, presented in Table 2, indicate that olefinic diols with 10 or less carbons are poor surfactants and the cis isomer has slightly better equilibrium surface tension than the trans isomer.

TABLE 2

Equilibrium Surface Tension (dynes/cm)

| | Structure | MOLECULAR FORMULA | CIS | TRANS |
|---|---|---|---|---|
| 1 | (structure) | $C_8H_{16}O_2$ | 62 | 64 |
| 2 | (structure) | $C_{10}H_{20}O_2$ | 51 | 59 |

EXAMPLES 3, 4 AND 5

Olefinic Diols with 18 or 20 Carbons

In Examples 3 and 4, trans-3-Hexene-2,5-dione (4.5 mmol) (prepared according to the procedure in *Tetrahedron Letters*, 1990, p. 7669) and 20 ml of tetrahydrofuran were cooled in a dry ice/isopropanol bath. Alkyl lithium (9.0 mmol) was added dropwise over 30 minutes. Reaction mixtures were stirred 15 minutes then quenched with aqueous ammonium chloride and products were extracted with ethyl ether. The ether layer was dried over magnesium sulfate, filtered and removed by rotary evaporation. The ratio of the GC area % for the reaction products are given in Table 3. The products were purified by column chromatography.

TABLE 3

Ratio of GC Area Percent for Reaction Products

| Example | Alkyl Group | 1,4 Addition | Mono-ol | Diol |
| --- | --- | --- | --- | --- |
| 3 | n-hexyl | 1 | 4.6 | 7.5 |
| 4 | phenyl | 1.8 | 1 | 2.5 |

In Example 5, diethyl fumarate (3.0 mmol) and tetrahydrofuran (10 ml) were cooled in a dry ice/isopropanol bath. Butyl lithium (18 mmol) was added dropwise over 60 minutes. Reactions were stirred 15 minutes then quenched with aqueous ammonium chloride and extracted with ethyl ether. The ether layer was dried over magnesium sulfate, filtered and removed by rotary evaporation. The product was purified by column chromatography eluting with 1:1 hexane:ethyl acetate.

The equilibrium surface tension of the compounds of Examples 3, 4 and 5 was measured 0.05 wt. %. The results are summarized in Table 4.

TABLE 4

| | | MOLECULAR FORMULA | EST (DYNES/CM) TRANS OLEFIN |
| --- | --- | --- | --- |
| 3 | 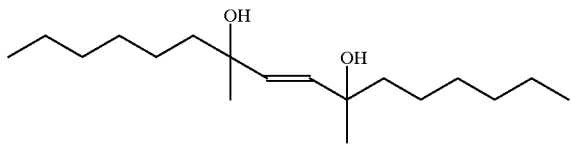 | $C_{18}H_{36}O_2$ | 67 |
| 4 | 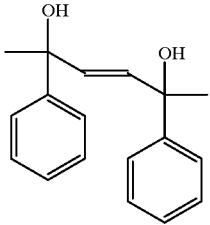 | $C_{18}H_{20}O_2$ | 67 |
| 5 | 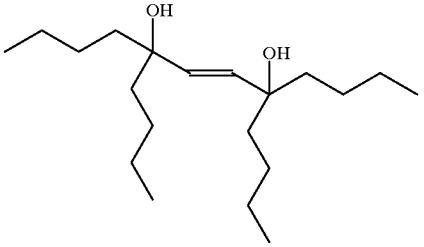 | $C_{20}H_{40}O_2$ | 69 |

The results show that trans olefinic diols with 18 or 20 carbon atoms have very poor equilibrium surface tension properties.

EXAMPLES 6–9

Olefinic Diols with 12 and 14 Carbon Atoms

The compounds of Examples 6 through 8 were prepared according to the procedure of Examples 1 and 2. Table 5 shows the GC area percent of products. The compound of Example 9 was prepared according to the procedure of Examples 3 and 4. The ratio of GC area percent of reaction products for the compound of Example 9 is presented in Table 6.

TABLE 5

| Example | Structure | Molecular Formula | Cis | Trans | Alkane |
|---|---|---|---|---|---|
| 6 | (structure) | $C_{12}H_{24}O_2$ | 88 | 8 | 3 |
| 7 | (structure) | $C_{12}H_{24}O_2$ | 83 | 9 | 6 |
| 8 | (structure) | $C_{14}H_{28}O_2$ | 78 | 16 | 4 |

TABLE 6

| Example | Structure | 1,4-Addition | Mono-ol | Diol |
|---|---|---|---|---|
| 9 | (structure) $C_{12}H_{24}O_2$ | 1 | 3.6 | 5 |

EXAMPLE 10

Water Solubility and Equilibrium Surface Tension (EST) of cis and trans isomers of C12 and C14 Olefinic Diols Water solubility and EST of the cis and trans isomers of Examples 6–9 were determined and the results are presented in Table 7, below. The data show that trans-isomers have a much higher water solubility and a better EST than the cis-isomers.

TABLE 7

| Example | Compound | Isomer | EST of 0.1 wt % solution (dynes/cm) | Solubility Limit (wt % in water) |
|---|---|---|---|---|
| 6 | (structure) $C_{12}H_{24}O_2$<br>3,6-diethyl-4-octene-3,6-diol | cis | 54 | 0.01 |
|   |   | trans | 50 | 0.5 |

TABLE 7-continued

| Example | Compound | Isomer | EST of 0.1 wt % solution (dynes/cm) | Solubility Limit (wt % in water) |
|---|---|---|---|---|
| 7 | 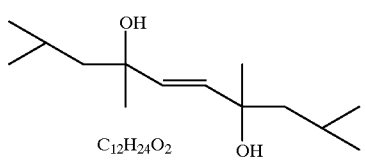 C₁₂H₂₄O₂ | cis | 58 | <0.01 |
|  | 2,4,7,9-tetramethyl-5-decene-4,7-diol | trans | 34 | 0.2 |
| 8 | 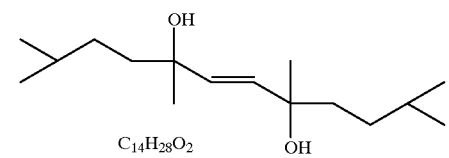 C₁₄H₂₈O₂ | cis | 68 | <0.01 |
|  | 2,5,8,11-tetramethyl-6-dodecene-5,8-diol | trans | 33 | 0.03 |

EXAMPLE 11
EST at Solubility Limit of trans-Olefinic Diols

The EST at the solubility limit of the trans-1,4-olefinic diols of Examples 7–9 was measured and the results are presented in Table 8 below. The data show that the trans isomers have superior EST at their solubility limits.

TABLE 8

| Example | Compound | EST at Solubility Limit (dynes/cm) | Solubility Limit (wt % in water) |
|---|---|---|---|
| 7 | 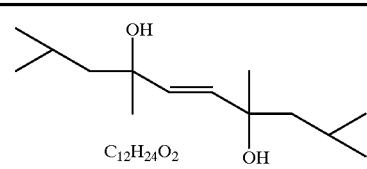 C₁₂H₂₄O₂ trans isomer | 29 | 0.2 |
| 8 | 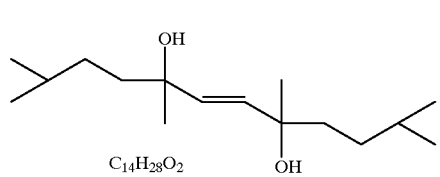 C₁₄H₂₈O₂ trans isomer | 33 | 0.03 |
| 9 | 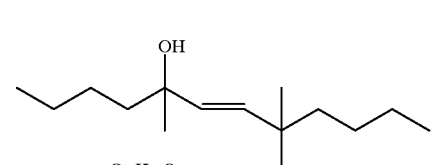 C₁₄H₂₈O₂ | 33 | 0.1 |

What is claimed is:

1. An aqueous composition comprising an organic compound and an effective amount of a trans isomer of an olefinic diol for reducing the equilibrium surface tension of the aqueous composition, the trans olefinic diol having the structural formula:

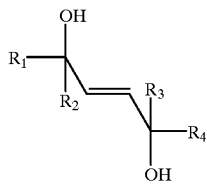

wherein each of $R_1$, $R_2$, $R_3$, and $R_4$ is the same or a different C1 to C9 linear or branched alkyl group and the total number of carbon atoms in the trans olefinic diol is between 12 and 17.

2. The aqueous composition of claim 1 wherein the equilibrium surface tension of the composition is 50 dynes/cm or less at the solubility limit of the trans olefinic diol and the total number of carbon atoms in the trans olefinic diol is between 14 and 16.

3. The aqueous composition of claim 1 wherein the equilibrium surface tension of the composition is 35 dynes/cm or less at the solubility limit of the trans olefinic diol.

4. The aqueous composition of claim 1 wherein $R_1$ and $R_4$ are each an alkyl C4 to C6 group and $R_2$ and $R_3$ are methyl groups.

5. The aqueous composition of claim 1 wherein $R_1$, $R_2$, $R_3$ and $R_4$ are ethyl groups.

6. In a method for applying a water-based composition to a surface, the composition containing an organic compound and an effective amount of a surfactant for reducing the equilibrium surface tension of the composition, the improvement which comprises employing as the surfactant a trans olefinic diol having the structural formula:

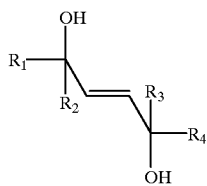

wherein each of $R_1$, $R_2$, $R_3$, and $R_4$ is the same or a different C1 to C9 linear or branched alkyl group and the total number of carbon atoms in the trans olefinic diol is between 12 and 17.

7. The method of claim 6 wherein the equilibrium surface tension of the composition is 50 dynes/cm or less at the solubility limit of the trans olefinic diol and the total number carbon atoms in the trans olefinic diol is between 14 and 16.

8. The method of claim 6 wherein the equilibrium surface tension of the composition is 35 dynes/cm or less at the solubility limit of the trans olefinic diol.

9. The method of claim 6 wherein $R_1$ and $R_4$ are each an alkyl C4 to C6 group and $R_2$ and $R_3$ are methyl groups.

10. The method of claim 6 wherein $R_1$, $R_2$, $R_3$ and $R_4$ are ethyl groups.

11. A method for reducing the equilibrium surface tension of a water-based organic-containing composition comprising combining the water-based organic-containing composition with an equilibrium surface tension reducing effective amount of a trans isomer of an olefinic diol having the formula:

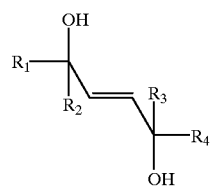

wherein each of $R_1$, $R_2$, $R_3$, and $R_4$ is the same or a different C1 to C9 linear or branched alkyl group and the total number of carbon atoms range from 12 to 17.

12. The method of claim 11 wherein the equilibrium surface tension of the combination of water-based organic-containing composition and trans isomer of an olefinic diol is 40 dynes/cm or less at the solubility limit of the trans olefinic diol.

13. The method of claim 11 wherein the equilibrium surface tension of the combination of water-based organic-containing composition and trans isomer of an olefinic diol is 35 dynes/cm or less at the solubility limit of the trans olefinic diol.

14. The method of claim 11 wherein $R_1$, $R_2$, $R_3$, and $R_4$ are ethyl.

15. The method of claim 11 wherein $R_1$ and $R_4$ are each an alkyl C4 to C6 group and $R_2$ and $R_3$ are each methyl.

16. The method of claim 11 wherein the total number of carbon atoms is between 14 and 16.

* * * * *